United States Patent [19]

De Laage De Meux et al.

[11] Patent Number: 5,683,408
[45] Date of Patent: Nov. 4, 1997

[54] SURGICAL PUNCH FORCEPS INSTRUMENT FOR EYE SURGERY

[75] Inventors: Patrice De Laage De Meux, Paris; Philippe Crozafon, Nice, both of France

[73] Assignee: Moria S.A., Paris, France

[21] Appl. No.: 537,851
[22] PCT Filed: Nov. 9, 1994
[86] PCT No.: PCT/FR94/01311
§ 371 Date: Nov. 15, 1995
§ 102(e) Date: Nov. 15, 1995
[87] PCT Pub. No.: WO95/13036
PCT Pub. Date: May 18, 1995

[30] Foreign Application Priority Data

Nov. 10, 1993 [FR] France ............ 93 13439

[51] Int. Cl.⁶ ........................................ A61B 17/14
[52] U.S. Cl. ................................... 606/184; 606/167
[58] Field of Search ........................ 606/107, 159, 606/1, 166, 167, 170–180, 184, 185; 128/749, 751, 754

[56] References Cited

U.S. PATENT DOCUMENTS

| | | |
|---|---|---|
| 4,509,516 | 4/1985 | Richmond . |
| 4,667,684 | 5/1987 | Leigh .................... 128/754 |
| 5,171,257 | 12/1992 | Ferzli .................... 606/205 |

FOREIGN PATENT DOCUMENTS

| | | |
|---|---|---|
| 0244491 | 11/1987 | European Pat. Off. . |
| 0517252 | 12/1992 | European Pat. Off. . |
| 8518482 | 9/1985 | Germany . |
| 2022421 | 12/1979 | United Kingdom . |
| 8203168 | 9/1982 | WIPO . |
| 9108784 | 6/1991 | WIPO . |

OTHER PUBLICATIONS

Database WPI Section PQ, Week 9319, Derwent Publications Ltd., London, GB. Class P, AN 93–157600 & SU A 1 734 735 (Eye Microsurgery Res. cité dans la demande.

Database WPI Section PQ, Week 9411, Derwent Publications Ltd., London, GB Class P, AN 94–08999 & SU A 2 003 353 (Don Med. Inst.).

*Primary Examiner*—Glenn K. Dawson
*Attorney, Agent, or Firm*—Sixbey Friedman Leedom & Ferguson; Gerald J. Ferguson, Jr.; Thomas W. Cole

[57] ABSTRACT

The invention relates to a surgical instrument of the punch forceps type, designed to perform trabeculectomy, the instrument including an elongate body (101) on which an elongate lever (102) is hinged, and a punch (110) constituted by a tubular blade (120) and a cutting plunger (130). According to the invention, the tubular blade (120) of the punch (110) is mounted to be forwardly inclined so as to define an obtuse angle (a) with the body (101) lying essentially in the range 95° to 160°, and the notch in the cutting plunger (130) of the punch (110) has a cutting edge (134) which is raised so as to be capable of engaging the tissue to be cut when said plunger is withdrawn. The punch (110) is preferably mounted so as to be interchangeable, thereby making it possible to have a cutting plunger that is interchangeable or suitable for single use.

8 Claims, 4 Drawing Sheets

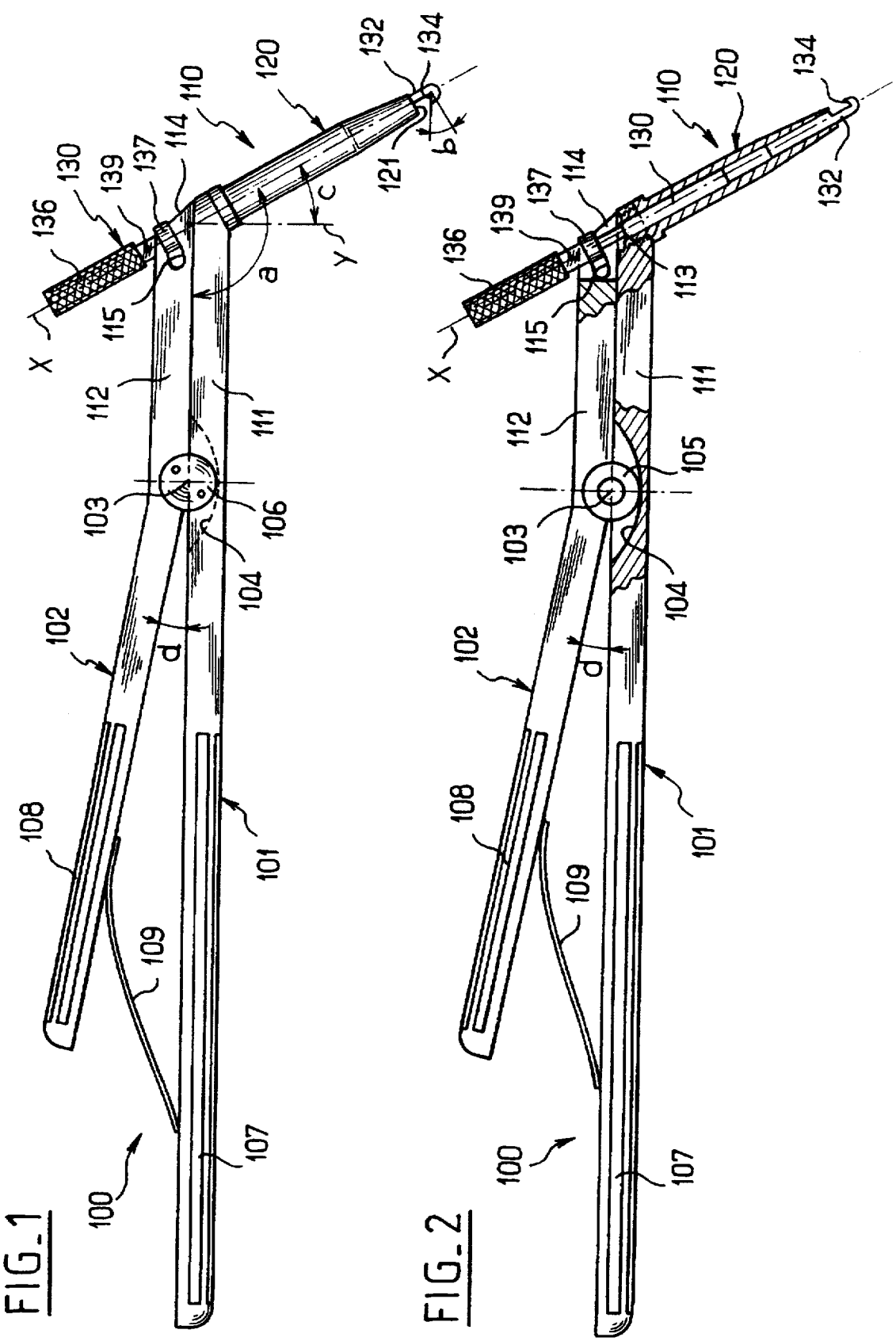

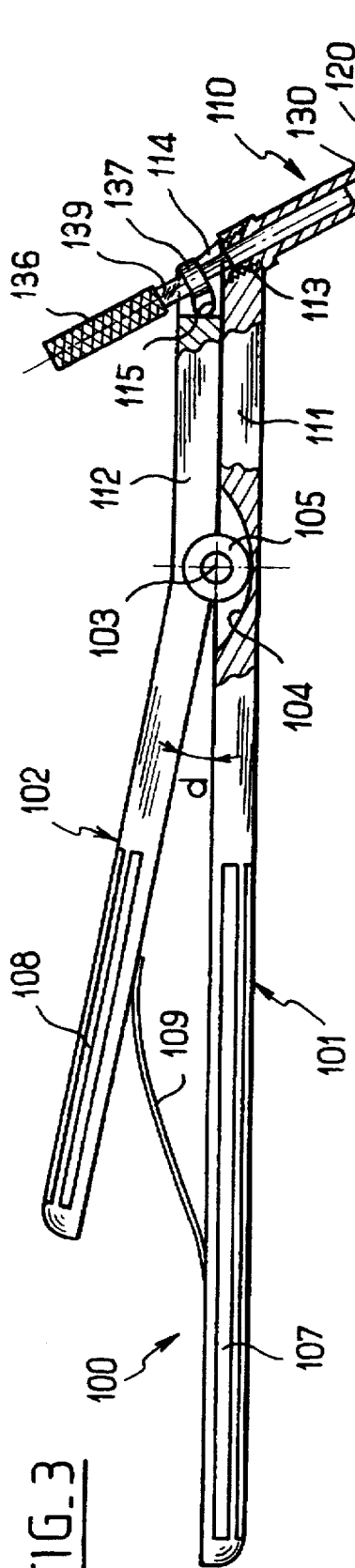

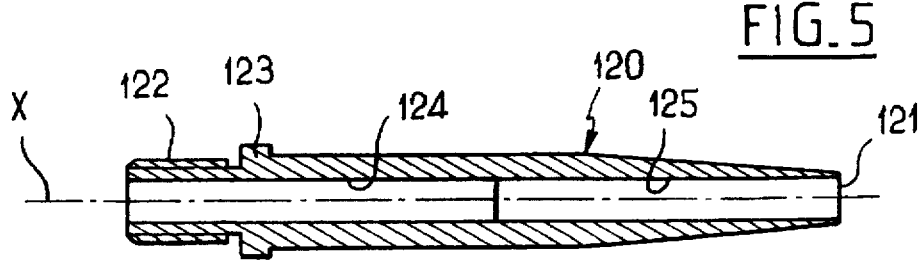
FIG_5
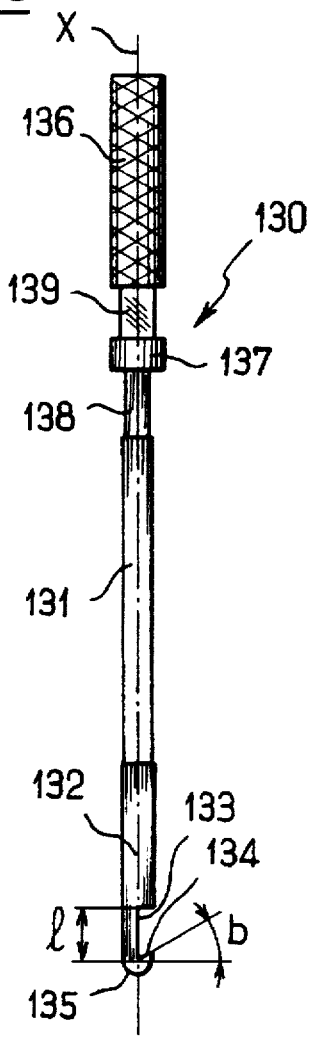
FIG_6
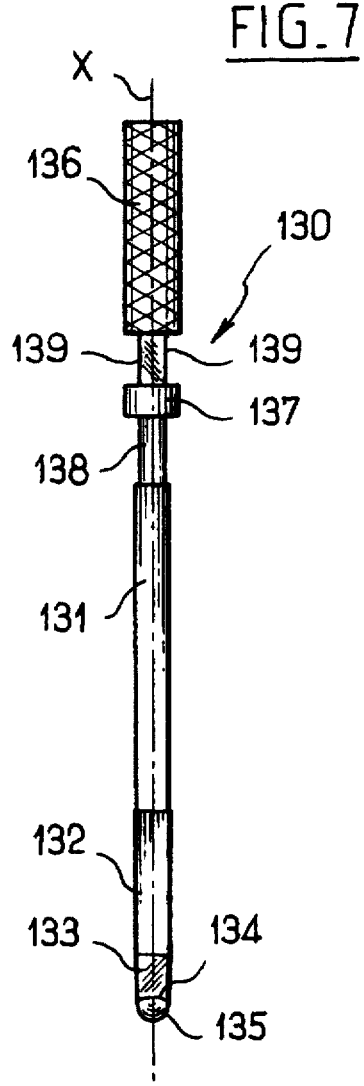
FIG_7
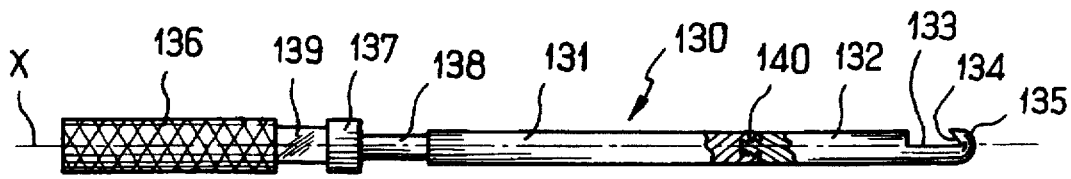
FIG_8

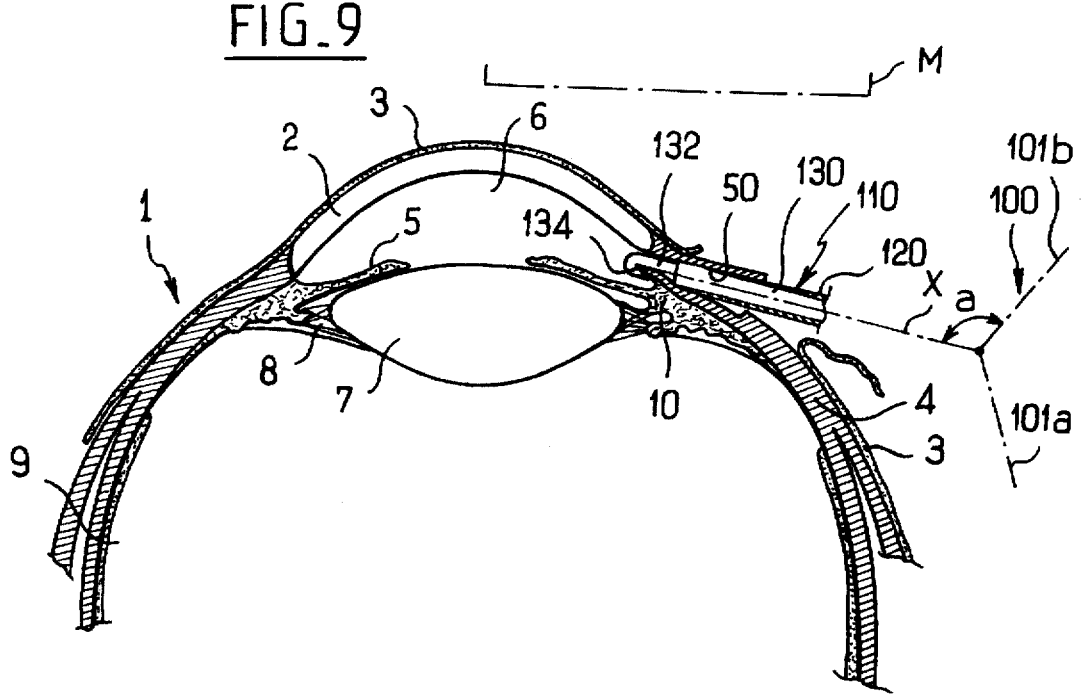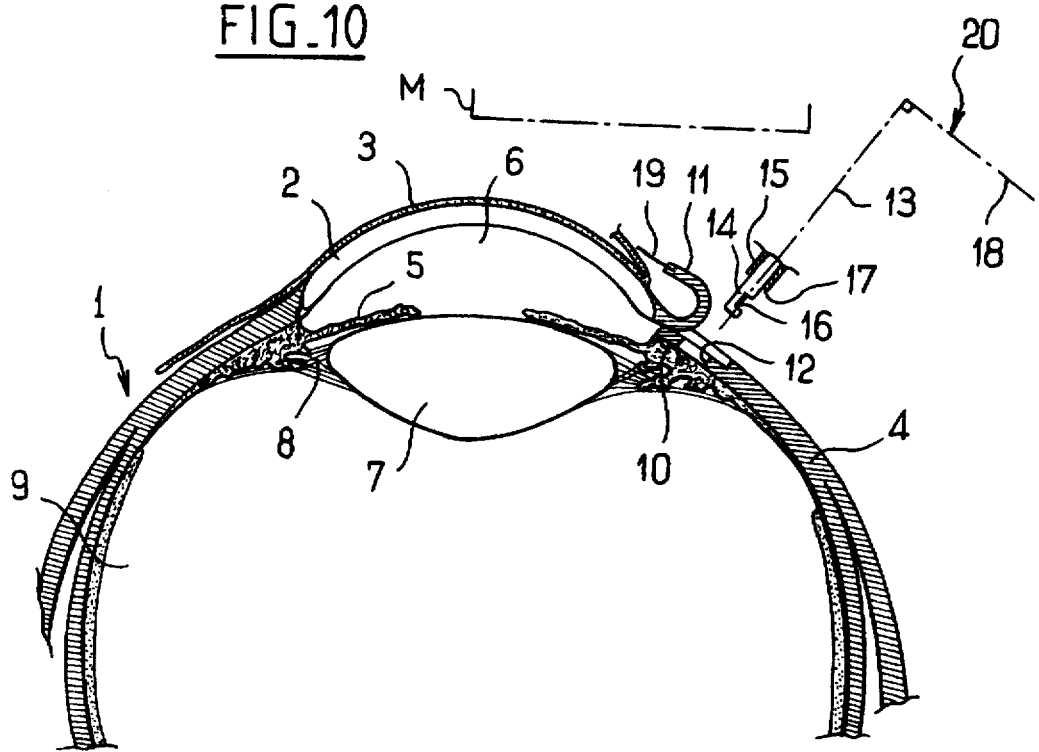

5,683,408

SURGICAL PUNCH FORCEPS INSTRUMENT FOR EYE SURGERY

This application is a 371 of PCT/FR94/01311, filed on Nov. 9, 1994.

The invention relates to the field of surgical instruments, and more particularly to instruments of the punch forceps type for eye surgery, for the purpose of performing trabeculectomy in association with a cataract operation.

Trabeculectomy is a surgical act that is frequently performed when treating glaucoma.

Glaucoma or hypertension of the eye is a serious eye disease that gives rise to an increase in the pressure within the eyeball due to excessive secretion of aqueous humor or to insufficient natural drainage thereof. This complaint constitutes the major cause of blindness, so treatment thereof is under continuous research.

The treatment of glaucoma is generally purely medical to begin with (using substances such as beta-blockers), but the way in which the pathology progresses often leads to the surgical solution of performing trabeculectomy.

Trabeculectomy is also often associated with a cataract operation even though the two complaints are due to causes that are very different. Under such circumstances, the operation consists initially in performing the cataract operation, and then in proceeding with trabeculectomy.

In general, trabeculectomy is a surgical operation that consists in perforating the trabeculum, so as to allow the aqueous humor under excess pressure within the anterior chamber of the eye to flow out therethrough, thus regulating intraocular pressure.

The traditionally-used technique consists in opening the conjunctiva and in making a flap or trap-door in the sclera so as to be able to perforate the trabeculum (see for example documents WO-A-82 03168 and SU-A-1 734 735).

In general, this ablation is performed by means of a sharp instrument such as a scalpel, a chisel, or punch forceps, which instrument is often referred to by the person skilled in the art as a "punch".

The punch used under such circumstances comprises an elongate body having an elongate lever hinged thereto together with a punch proper constituted by a tubular blade rigidly fixed to the end of the body and a plunger that slides within the tubular blade, the distal end of the plunger having a notch with a cutting edge and having its proximal end engaged with the end of the lever.

Return is provided in the forceps by means of a spring blade urging the forceps to a rest position in which the operating handles (behind the hinge) are spaced apart: in this position, the notch having a cutting edge projects beyond the circular cutting edge of the tubular blade. When the surgeon clamps the operating handles together, the lever retracts the cutting plunger into the inside of the tubular blade, and tissue is clamped between the circular cutting edge of the tubular blade and the cutting edge of the notch in the cutting plunger, thereby cutting the tissue.

It should be observed that this type of punch is designed to perform perforation together with cutting out, and therefore differs considerably from punches used in other fields of surgery and designed for taking samples or fragments of bone (with such punches being described, for example, in documents EP-A-0 244 491, GB-A-2 022 421, and DE-U-85 18 482).

Accompanying FIG. 10 shows the usual trabeculectomy procedure using a punch of the above-specified type.

This figure shows an eye 1 together with its cornea 2 covered in conjunctiva 3, and associated with its sclera 4.

There can also be seen the iris 5, the anterior chamber 6 occupied by aqueous humor, the lens 7, and the zonula 8 attached thereto, together with the posterior chamber 9 occupied by the vitreous humor. The annular zone 10 includes the zonular muscles and the trabeculum.

After opening the conjunctiva, the surgeon then cuts a flap 11 of side 5 mm to 7 mm in the outer thickness of the sclera, and installs a thread 19 to hold the flap open. A window 12 is then cut through the inner thickness of the sclera so as to give access to the tissues of the trebeculum. Using forceps (not shown) a portion of the trebeculum is withdrawn and then cut by means of scissors, or as shown in the present case by means of a punch 20.

The axis of the punch is referenced 13 and is embodied by a tubular blade 15 having a cutting free edge 17 associated with a cutting plunger 14 which is terminated by a notch having a cutting edge 16. The direction in which the body of the instrument 20 extends is represented by chain-dotted line 18.

It should be observed that the axis 13 is perpendicular to the direction 18 and that the cutting edge 16 of the cutting plunger is straight, i.e. perpendicular to the axis of the plunger.

The surgeon must work under a microscope (reference M), thereby, de facto, limiting access to the zone in which the operation takes place. As a result, the surgeon is somewhat constrained in positioning and handling the instrument, and the direction in which the punch makes its approach is then essentially orthogonal, as shown in FIG. 10.

Trabeculectomy may optionally be followed by iridectomy, after which the surgeon closes the flap in the sclera and performs a suture.

The above intervention is difficult and continues to be relatively traumatic for the patient. The amount of suturing is also considerable.

It would be advantageous to be able to obtain access to the trabeculum in a different manner in order to make a perforation therein, however the geometry of the tool and the presence of the microscope serve in practice to prevent any other access path being considered.

The invention seeks specifically to solve the above problem by providing a surgical instrument enabling trabeculectomy to be performed without requiring a scleral flap to be made.

The invention thus seeks to provide a surgical instrument of the punch forceps type and of a structure that makes it possible to perform trabeculectomy in a manner that is simple and relatively untraumatic, by passing through a tunnel incision of the type made for performing a cataract operation.

More particularly, the invention provides a surgical instrument of the forceps punch type for eye surgery, being designed to perform trabeculectomy, the instrument having an elongate body on which an elongate lever is hinged, together with a punch constituted by a tubular blade rigidly fixed to the end of the body and by a cutting plunger slidably mounted in said tubular blade, the distal end of the plunger having a notch with a cutting edge and the proximal end of the plunger being connected to the end of the lever, the instrument being characterized in that:

the tubular blade of the punch is mounted so as to be forwardly inclined, thereby defining an obtuse angle relative to the body lying essentially in the range 95° to 160°; and the notch of the cutting plunger of the punch has a cutting edge which is raised, so as to enable it to hook onto the tissue to be cut when said plunger is withdrawn.

Preferably, the axis X of the tubular body is rectilinear and lies in the midplane of the instrument which is orthogonal to the hinge axis of the lever, and the axis of the tubular blade forms an angle of about 120° with the general direction in which the body extends.

This makes assembly simple and accurate by providing for the body to have end tapping for releasably securing the tubular blade, the axis of said tapping coinciding with the axis of said blade.

Also advantageously, the cutting edge of the notch of the cutting plunger is raised relative to the orthogonal to the axis of the plunger through an angle lying essentially between 15° and 60°, and preferably about 30°.

It is also advantageous for the cutting edge of the notch to be held in the midplane of the instrument by guidance associated with the means for fastening the proximal end of the cutting plunger to the lever.

In an advantageous embodiment, the lever is terminated by two fins disposed on either side of the midplane of the instrument, each of these two fins having a respective curved open-ended notch forming the means for fastening the proximal end of the cutting plunger by co-operation between these two notches and a cylindrical projection on the plunger which passes between said fins.

It is then advantageous for the cutting plunger to have two guidance facet-forming flats on either side of its axis that co-operate with the two fins of the lever, the cutting edge of the notch of the plunger then being capable of being disposed in one or other of two symmetrical positions relative to the axis of said plunger.

According to another advantageous characteristic, the cutting plunger is interchangeable, at least in part, and suitable for discarding after single use. For example, the distal end of the cutting plunger is an add-on endpiece which constitutes an interchangeable part for single use.

Other characteristics and advantages of the invention appear more clearly in the light of the following description and the accompanying drawings, that relate to a particular embodiment and in which FIG. 1 is an elevation view of a surgical instrument of the invention in its rest position (cutting edge projecting from the cutting edge of the tubular blade);

FIGS. 2 and 3 are two similar views in partial section in the hinge zone and of the punch proper, showing two possible ways in which the cutting edge may be directed relative to the body of the instrument;

FIG. 4 shows an active position of the above instrument;

FIG. 5 is an axial section on a larger scale of the tubular blade of the above-specified instrument;

FIGS. 6 and 7 are two elevation views (at 90° to each other) of the cutting plunger of the same instrument, serving in particular to show more clearly the two guide flaps in the hooking zone of said plunger;

FIG. 8 shows a variant cutting plunger having an add-on endpiece; and

FIG. 9 is similar to FIG. 10 which is described above with respect to the prior art, and shows how the trabeculectomy technique of the invention is implemented using a surgical instrument of the present invention.

In FIG. 1, there can be seen a punch forceps type instrument 100 of the invention, comprising an elongate body 101 having an elongate lever 102 hinged thereto, the hinge axis being referenced 103. The rear portions of the body and of the lever, respectively referenced 107 and 108, form operating handles, while the front portions 111 and 112 serve for mounting the associated punch 110. As can be seen more clearly in FIGS. 2 and 3, the lever 102 has a central disk 105 which is received in an associated slot 104 of the body 101 between two lateral lugs (not shown herein) of said body, with the assembly being held together by a screwed-on hub 106. This mounting guarantees that the two moving elements are held in a common midplane which is orthogonal to the hinge axis of the lever. The surgical instrument 100 is urged towards its rest position by a spring blade 109 or by any equivalent means. In this position, the rear handles 107 and 108 are an angle d apart, which angle is naturally a function of the length of the lever arms and of the stroke of the cutting plunger of the punch, and an average value will generally lie in the range 15° to 45°. The front portions 111 and 112 touch each other in this case in the rest position.

The surgical instrument 100 also includes a punch 110 constituted by a tubular blade 120 rigidly secured to the end of the body 101, and by a cutting plunger 130 slidably mounted in said tubular blade, the distal end of the plunger having a notch with a cutting edge while the proximal end thereof is hooked to the end of the lever 102.

According to a first characteristic of the invention, the tubular blade 120 of the punch 110 is mounted so as to be forwardly inclined, thereby defining an obtuse angle relative to the body 101, which angle lies essentially in the range 95° to 160°. In the present case, the axis X of the tubular blade 120 is rectilinear, lying in the midplane of the instrument which is orthogonal to the hinge axis of the lever 102, and the axis X is at an angle a of about 120° to the general direction in which the body 101 extends.

As can be seen more clearly in FIGS. 2 to 4, the body 101 has end tapping 113 for releasably securing the tubular blade 120, the axis of said tapping naturally coinciding with the axis X of the tubular blade. Naturally this particular type of mounting could be replaced by any other means that guarantee proper orientation of the punch, and that enable punches to be interchangeable.

Thus, the punch of the surgical instrument of the invention is forwardly inclined at an angle c beyond a perpendicular direction Y which used to be the direction of surgical instruments in the prior art, with the angle c lying in the range 5° to 70°, and being about 30° in the present case.

This first angle between the axis of the punch and the general direction of the body of the instrument makes it possible to envisage performing trabeculectomy through a tunnel incision of the type used for performing a cataract operation.

In FIG. 9, the various portions of the eye referenced 1 to 10 correspond to the portions already described above with reference to FIG. 10. However, it can be seen that after making an opening through the conjunctiva 3, the surgeon has made a tunnel incision 50 of the type normally performed for a cataract operation, and that this has been done by using a diamond cutter (not shown) having a width that calibrates the incision (generally lying in the range 2.8 mm to 3.2 mm). The tunnel incision 50 is made so as to open out into the anterior chamber 6 of the eye. The surgeon can then install the surgical instrument 100 of the invention in either of the two positions 101a and 101b for the body of said instrument so as to have the instrument ready to hand. In FIG. 9, the presence of the body of the instrument is represented merely by chain-dotted lines, but there can be seen the terminal portion of the punch 110 as described above which has been inserted in the tunnel incision 50. The punch is thus advanced into the tunnel incision until the distal end 132 of the cutting plunger of the instrument penetrates into the anterior chamber 6. It is important to observe that during such installation, the surgeon is operating blind insofar as the sclera 4 is opaque and all the surgeon can see, in the limit, is the end of the cutting plunger as seen through the cornea. This naturally makes the cutting operation more difficult, since the surgeon must arrange things so as to be able to grasp the tissue to be cut without exerting any tension on the cataract incision.

According to the invention, this problem is solved by a second essential characteristic of the invention whereby the notch of the cutting plunger 130 of the punch has a cutting edge 134 that is raised, so as to be able to engage the tissue to be cut when said plunger is withdrawn. Thus, the cutting edge is no longer a straight edge as in the prior art, but is a raised edge forming a kind of fish-hook suitable for catching the tissue to be cut during withdrawal of the cutting plunger. Because of this hooking action, the surgeon can perform accurate cutting out in the inside wall of the sclera and the trabeculum, in spite of being unable to monitor the cutting through the microscope M. Once trabeculectomy has been terminated, the surgeon then merely needs to withdraw the punch and to close the tunnel incision in the sclera, which incision is so small that it is possible to envisage omitting any suturing for the purpose of closing it. The intervention is thus considerably simplified, and it is much less traumatic for the patient; in addition, suturing is minimized or even unnecessary insofar as use is made of a tunnel incision having a width of about 2.5 mm.

The surgical instrument of the invention can thus be used for isolated anti-glaucoma action by means of trabeculectomy, or for use after a cataract operation, e.g. by phacomulsification, in which case it makes use of a tunnel incision that has already been provided for the preliminary operation.

The surgeon can thus perform trabeculectomy that is isolated, or that is subsequent to a cataract operation, by making a tunnel incision in the upper part of the eye, so that the surgeon is well placed for engaging the surgical instrument insofar as the surgeon is located behind the head of the patient in the prone position.

In the prior art, it has been general to make a tunnel incision in the upper portion of the eye for a cataract operation, whereas for trabeculectomy, it has been the practice to provide a scleral flap beneath the cornea: in this respect, the invention provides a very considerable improvement. Naturally, if necessary, iridectomy can be performed before reclosing the linear tunnel incision in the sclera. The instrument of the invention thus makes it possible instantly to perform a protected filtering operation analogous to trabeculectomy by inserting the punch into the anterior chamber of the eye and by moving back a little so as to catch the ceiling plane of the peripheral cornea, and then making a precalibrated semicircular cut having a diameter of about 1.7 mm without it being necessary to change the position of the instrument.

The angle of the punch makes the operation easy for the surgeon and facilitates great accuracy in performance (the body of the instrument is generally upwardly directed, as represented by position 101b in FIG. 9). The special geometry for the distal end of the cutting plunger thus facilitates non-traumatic and direct insertion into the anterior chamber without there being any need to lift a trap-door in the sclera. The special shape of the cutting portion of the cutting plunger ensures reliably that it is in contact with the iridocorneal angle, and it ensures that the amount of scleracorneal tissue that is excised is always the same.

FIGS. 5 to 7 show the structure of the tubular blade 120 and of the cutting plunger 130 of the above-described surgical instrument in greater detail.

The tubular blade 120 has a central bore constituted in this case by two colinear portions 124 and 125 terminating in a free cutting edge 121 at the distal end. At the proximal end, there is a threaded endpiece 122 suitable for installing the blade at the end of the body of the instrument, and the thread is associated with an abutment collar 123.

The cutting plunger 130 comprises a cylindrical central body 131 running into a distal end 132 having a notch 133 whose cutting edge 134 is raised through an angle b, which, as mentioned above, may lie essentially in the range 15° to 60°, and is preferably about 30°. The angle b must be sufficient to hook onto the tissue that is to be cut, but it must not be too great, in order to avoid hooking onto other tissue during cutting. The height 1 of the notch 133 is preferably about 1 mm to 3 mm in practice: a larger notch should be avoided so as to avoid having a stroke that is too long since that would run the risk of touching the iris or of damaging tissue behind. From this point of view, it should be observed that the terminal end 135 of the cutting plunger 130 has a rounded nose-cone shape that facilitates gentle insertion without running the risk of cutting any tissue.

It is also important for the cutting edge 134 of the notch to be capable of being retained in the midplane of the instrument so as to avoid any inaccuracy during cutting. According to the invention, this is achieved by guidance associated with the means for fastening the proximal end of the cutting plunger to the lever. If reference is made to FIGS. 1 to 4, it can be seen that the lever 102 is terminated by two fins 114 disposed on either side of the midplane of the instrument, each of these two fins having a curved and open-ended notch 115 that forms the fastening means for the proximal end of the cutting plunger by co-operation between the two notches 115 and a cylindrical projection 137 on the plunger which passes between the fins. The fastening of the cylindrical projection 137 guarantees accuracy in the axial movement of the cutting plunger when the surgeon clamps together the two operating handles of the instrument. To maintain an accurate and stable angular position, provision is made (as can be seen more clearly in FIGS. 6 and 7) for the cutting plunger 130 to present two flats 139 on either side of its axis X, which flats guide facets by co-operating with the inside faces of the two fins 114 of the lever 102. As shown in FIGS. 2 and 3, the cutting edge 134 of the notch of the plunger can then be disposed in one or other of two symmetrical positions relative to the axis of said plunger. To change this position, it suffices to dismount the tubular blade 120 by unscrewing it so as to disengage the cutting plunger 130, preferably by holding it via a knurled terminal portion 136, then to rotate the plunger through 180° about its own axis X, and finally to reinstall the tubular blade on the body of the instrument. Thus, the cylindrical projection 137 of the cutting plunger is bracketed at the top by the two guide flats 139 and at the bottom by a cylindrical portion 138 whose diameter corresponds to the distance between the two above-mentioned guide facets. This makes it possible to have constant spacing between the two inside faces of the fins 114.

As shown in FIG. 4, when the surgeon clamps the instrument 100 in the direction of arrow 200, the cutting plunger 130 is moved back along arrow 201, thereby achieving the desired cutting of tissue by the punch of said instrument.

It is also advantageous to provide for the cutting plunger 130 to be interchangeable, at least in part, and to be suitable for discarding after single use, i.e. for it to be a discardable component. By this procedure, it is guaranteed that the cutting edge will always be completely sharp, thus avoiding any tearing of tissue instead of cutting the tissue cleanly. Under such circumstances, the plunger may be made of a plastics material or of a soft metal. In a variant, as shown in FIG. 8, it is also possible to provide for the distal end 132 of the cutting plunger to be an add-on endpiece which constitutes an interchangeable part for single use, said endpiece being installed, for example, by screwing a threaded peg 140 into an associated tapped hole in the plunger body.

A surgical instrument is thus provided enabling trabeculectomy to be performed without requiring a flap to be made in the sclera, with the instrument passing through a tunnel incision of the type used for performing a cataract operation. The surgical instrument designed in this way is simple in structure and light in weight, it is easy to manipulate, and it can be manipulated with sufficient accuracy to enable the surgeon to operate confidently, even though the surgeon is operating "blind" when it comes to perforating the trabeculum.

The invention is not limited to the embodiment described above, but on the contrary it extends to any variant that uses equivalent means to reproduce the essential characteristics specified above.

We claim:

1. A surgical instrument of the forceps punch type for eye surgery, being designed to perform trabeculectomy, the instrument having an elongate body on which an elongate lever is hinged about a hinge axis, together with a punch constituted by an elongated tubular blade rigidly fixed to the end of the body and by a cutting plunger slidably mounted in said tubular blade, the distal end of the plunger having a notch with a cutting edge and the proximal end of the plunger being connected by fastening means to the end of the lever, wherein:

the tubular blade of the punch has a longitudinal axis which is rectilinear and lies in a midplane of the instrument that is orthogonal to the hinge axis of the lever, said tubular blade being furthermore mounted so as to have its longitudinal axis forwardly inclined, thereby defining an obtuse angle relative to the body lying essentially in a range 95° to 160° for enabling the performance of a trabeculectomy through a tunnel incision; and said body has an end tapping for dismountably securing the tubular blade, the axis of said tapping coinciding with the longitudinal axis of said blade, and wherein the cutting plunger has a terminal end of rounded shape for enabling gentle insertion of the punch when passing through a tunnel incision, and the notch of said cutting plunger has a cutting edge which is raised for enabling it to hook onto the tissue to be cut when said plunger is withdrawn.

2. A surgical instrument according to claim 1, characterized in that longitudinal axis of the tubular blade forms an angle of about 120° with the general direction in which the body extends.

3. A surgical instrument according to claim 1, characterized in that the cutting edge of the notch of the cutting plunger is raised relative to the orthogonal to the axis (X) of the plunger through an angle lying essentially between 15° and 60°.

4. A surgical instrument according to claim 1, wherein the means for fastening the proximal end of the cutting plunger to the lever further includes guiding means which hold the cutting edge of the notch of said cutting plunger in the midplane of the instrument.

5. A surgical instrument according to claim 1 wherein the means for fastening the proximal end of the cutting plunger to the lever consists of (i) two fins provided at a distal end of the lever on either side of the midplane of the instrument, each of these two fins having a respective curved open-ended notch and (ii) a cylindrical projection on the proximal end of the plunger which passes between said fins into both of said notches.

6. A surgical instrument according to claim 5, characterized in that the cutting plunger presents two guidance facet-forming flats on either side of its axis that cooperate with the two fins of the lever, the cutting edge of the notch of the plunger then being capable of being disposed in any one of two symmetrical positions relative to the axis of said plunger.

7. A surgical instrument according to claim 1, characterized in that the cutting plunger is interchangeable, at least in part, and suitable for single use.

8. A surgical instrument according to claim 7, wherein the cutting plunger has a distal end which is an add-on endpiece that constitutes an interchangeable part for single use.

* * * * *

UNITED STATES PATENT AND TRADEMARK OFFICE
CERTIFICATE OF CORRECTION

PATENT NO. : 5,633,408
DATED : Nov. 4, 1997
INVENTOR(S) : Patrice De Laage De Meux and Philippe Crozafon It is certified that error appears in the above-identified patent and that said Letters Patent is hereby corrected as shown below:

On the title page, item [73] Assignee, please delete "Moria S.A., Paris, France" and insert --Moria S.A. (1/3 interest)--.

Signed and Sealed this

Seventeenth Day of November, 1998

Attest:

BRUCE LEHMAN

Attesting Officer

Commissioner of Patents and Trademarks